United States Patent
Meingassner et al.

(10) Patent No.: US 7,414,074 B2
(45) Date of Patent: Aug. 19, 2008

(54) ANTIINFLAMMATORY LACTONES

(75) Inventors: Josef Gottfried Meingassner, Perchtoldsdorf (AT); Klaus Thirring, Wien (AT)

(73) Assignee: Novartis AG, Basel (CH)

( * ) Notice: Subject to any disclaimer, the term of this patent is extended or adjusted under 35 U.S.C. 154(b) by 104 days.

(21) Appl. No.: 10/594,098

(22) PCT Filed: Mar. 31, 2005

(86) PCT No.: PCT/EP2005/003384

§ 371 (c)(1), (2), (4) Date: Nov. 1, 2006

(87) PCT Pub. No.: WO2005/097771

PCT Pub. Date: Oct. 20, 2005

(65) Prior Publication Data

US 2007/0219143 A1    Sep. 20, 2007

(30) Foreign Application Priority Data

Apr. 1, 2004 (GB) .................. 0407466.2
Apr. 1, 2004 (GB) .................. 0407467.0

(51) Int. Cl.
*A61K 31/351*    (2006.01)
*C07D 309/38*    (2006.01)

(52) U.S. Cl. ................. 514/459; 514/460; 549/292

(58) Field of Classification Search ............. 514/459, 514/460; 549/292
See application file for complete search history.

(56) References Cited

U.S. PATENT DOCUMENTS 4,753,959 A    6/1988 Tscherter et al.

OTHER PUBLICATIONS

Parker et al., "Synthesis of Carba-beta-L-Fructopyranose and Carbacyclic Analogs og Topiramate, an Anticonvulsant Agent. p", Synlett., No. 12, pp. 2095-2098 (2004).

*Primary Examiner*—Taofiq A Solola

(57) ABSTRACT

Lactones of Formula (I) which are pharmaceutically active in diseases associated with inflammation

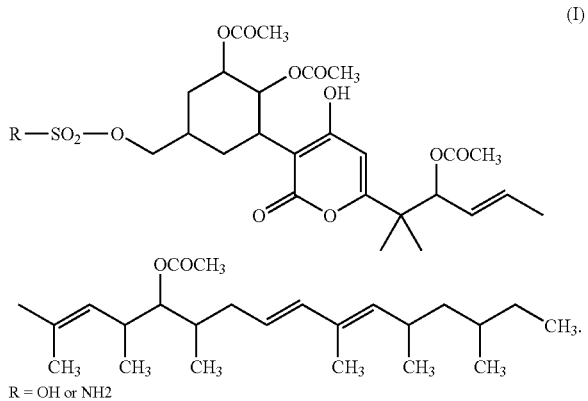

11 Claims, No Drawings

ANTIINFLAMMATORY LACTONES

The present invention relates to anti-inflammatory lactones.

In one aspect the present invention provides a compound of formula

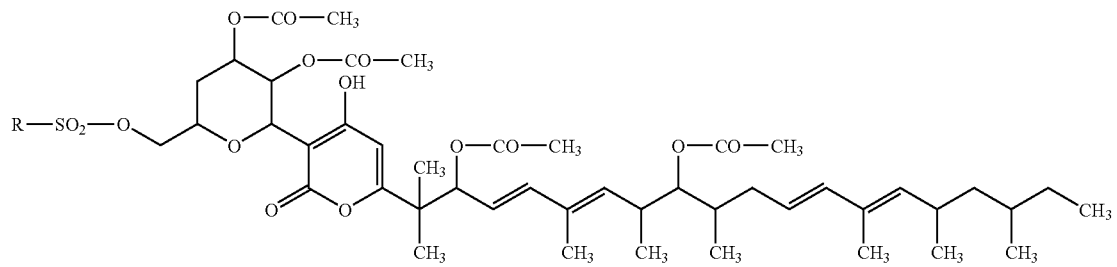

such as a compound of formula

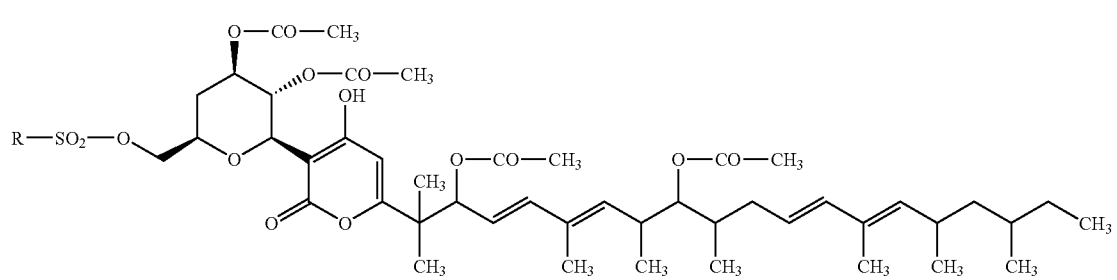

wherein R is hydroxy or amino.

A compound of formula I includes a compound of formula I'.

Preferably in a compound of formula I
R is hydroxy;
R is amino.

In another aspect the present invention provides a compound of the present invention which is selected from the group consisting of Acetic acid 7-acetoxy-1-[1-((2R,3R,4R,6R)-3,4-diacetoxy-4'-hydroxy-2'-oxo-6-sulfooxymethyl-3,4,5,6-tetrahydro-2.H.,2'.H.-[2,3']bipyranyl-6'-yl)-1-methyl-ethyl]-4,6,8,12,14,16-hexamethyl-octadeca-2,4,10,12-tetraenyl ester, e.g. including Acetic acid (2E,4E,10E,12E)-7-acetoxy-1-[1-((2R,3R,4R,6R)-3,4-diacetoxy-4'-hydroxy-2'-oxo-6-sulfooxymethyl-3,4,5,6-tetrahydro-2.H.,2'. H.-[2,3']bipyranyl-6'-yl)-1-methyl-ethyl]-4,6,8,12,14,16-hexamethyl-octadeca-2,4,10,12-tetraenyl ester, and Acetic acid 7-acetoxy-1-[1-(3,4-diacetoxy-4'-hydroxy-2'-oxo-6-sulfamoyloxymethyl-3,4,5,6-tetrahydro-2.H.,2'.H.-[2,3']bipyranyl-6'-yl)-1-methyl-ethyl]-4,6,8,12,14,16-hexamethyl-octadeca-2,4,10,12-tetraenyl ester, e.g. including Acetic acid (2E,4E, 10E, 12E)-7-acetoxy-1-[1-((2R,3R,4R,6R)-3,4-diacetoxy-4'-hydroxy-2'-oxo-6-sulfamoyloxymethyl-3,4,5,6-tetrahydro-2.H.,2'.H.-[2,3']bipyranyl-6'-yl)-1-methyl-ethyl]-4,6,8,12,14,16-hexamethyl-octadeca-2,4,10,12-tetraenyl ester.

Compounds provided by the present invention are hereinafter designated as "compound(s) of (according to) the present invention". A compound of formula I includes a compound of formula I'. A compound of the present invention includes a compound in any form, e.g. in free form, in the form of a salt, in the form of a solvate and in the form of a salt and a solvate.

In another aspect the present invention provides a compound of the present invention in the form of a salt.

Such salts include preferably pharmaceutically acceptable salts, although pharmaceutically unacceptable salts are included, e.g. for preparation/isolation/purification purposes. A salt of a compound of the present invention includes a metal salt, e.g. or, where appropriate an acid addition salt. Metal salts include for example alkali or earth alkali salts, preferably alkali, such as lithium, potassium, sodium, preferably sodium. A compound of the present invention in free form may be converted into a corresponding compound in the form of a salt; and vice versa. A compound of the present invention in free form or in the form of a salt and in the form of a solvate may be converted into a corresponding compound in free form or in the form of a salt in non-solvated form; and vice versa.

A compound of of the present invention may exist in the form of isomers and mixtures thereof; e.g. optical isomers, diastereoisomers, cis/trans conformers. A compound of the present invention may e.g. contain asymmetric carbon atoms and may thus exist in the form of enatiomers or diastereoisomers and mixtures thereof, e.g. racemates. Any substituent bound to an asymmetric carbon atom may be present in the (R)-, (S)- or (R,S)-configuration, preferably in the (R)- or (S)-configuration. For example, the tetrahydropyranyl ring and the nonadeca-alkenyl chain in a compound of formula I comprises asymmetric C-atoms and substitutents attached to such asymmetric C-atoms, such as sulfonyloxymethyl, methylcarbonyloxy, methyl groups, the pyranyl ring, may be in the (R)- or in the (S)-configuration, e.g. as set out in a compound of formula I' or in the selected group of compounds of the present invention. Additionally a compound of formula I comprises double bonds in the nonadeca-alkenyl chain and substituents bound to such a double bond may be cis- or trans-confomers. Preferably the configuration of substituents attached to asymmetric C-atoms of a compound of formula I and the confomers in a compound of formula I are the same as in a compound of formula I, if the starting material for its production, namely a compound of formula II (as set out below) is obtained by fermentation (see production process below).

Isomeric mixtures may be separated as appropriate, e.g. according, e.g. analogously, to a method as conventional, to obtain pure isomers. The present invention includes a compound of the present invention in any isomeric form and in any isomeric mixture. The present invention also includes tautomers of a compound of formula I, where tautomers can exist.

In another aspect the present invention provides a process for the production of a compound of formula I comprising sulfating or sulfamoylating a compound of formula In a preferred aspect of the present invention sulfation is carried out by reaction of a compound of formula II with $SO_3$-pyridine complex in organic solvent, e.g. polar organic solvent, such as N,N-dimethylformamide, and isolating a compound of formula I, wherein R is hydroxy from the reaction mixture;

sulfamoylation is carried out by treating of a compound of formula II with NaH and further treatment with $ClSO_2NH_2$ (e.g. obtainable by reaction of chlorosulfonyl isocyanate with formic acid) in organic solvent, e.g. polar organic solvent, such as N,N-dimethylformamide, and isolating a compound of formula I, wherein R is amino, from the reaction mixture. Salt formation may be carried out as appropriate, e.g. according, e.g. analogously to a method as conventional, e.g. for alkali or earth alkali metal salt formation a compound of formula I may be treated with a base of formula MET-OH or of formula MET'OH$_2$, wherein MET is an alkali ion and MET' is an earth alkali ion.

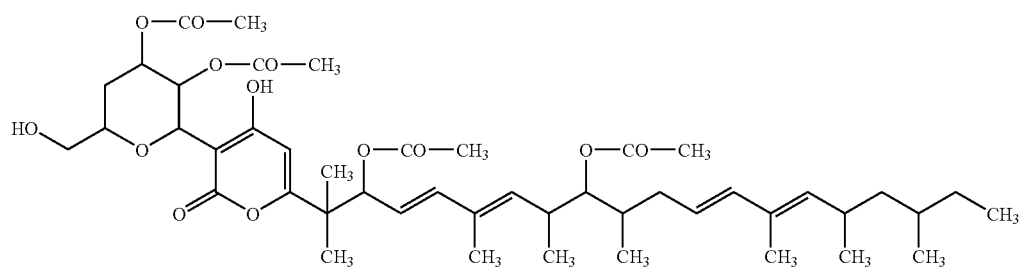

II such as a compound of formula

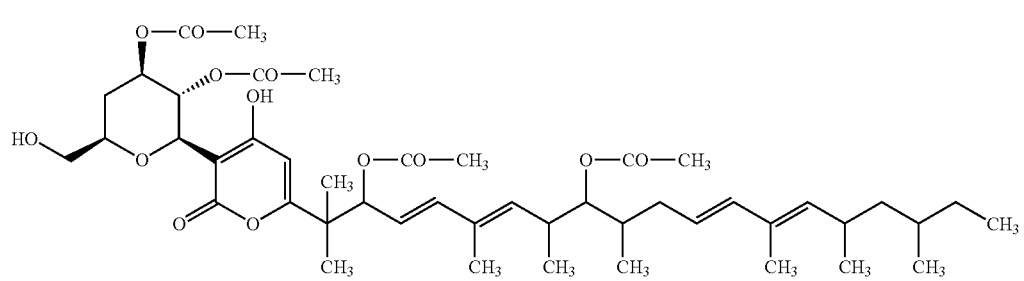

II' and isolating a compound of formula I obtained from the reaction mixture; and, optionally, converting a compound of formula I obtained in another compound of formula I, for example converting a compound of formula I obtained into a salt thereof, or, if a compound of formula I is obtained in the form of a salt, converting said salt into a free base of a compound of formula I.

A compound of formula II includes a compound of formula II'.

Sulfation or sulfamoylation may be carried out as appropriate, e.g. according, e.g. analogously, to a process as conventional.

In another aspect the present invention provides a compound of formula II, e.g. useful as an intermediate in the production of a compound of the present invention, e.g. in free base form or in the form of a salt, including salts as described above for a compound of the present invention.

A compound of formula II is herein designated also as "an intermediate of (according to) the present invention" in distinction to a compound of formula I "a compound of (according to) the present invention".

A compound of formula II may be obtained as appropriate, e.g. according, e.g. analogously, to a process as conventional, e.g. or as described herein.

In another aspect the present invention provides a process for the preparation of a compound of formula II, comprising acylating a compound of formula

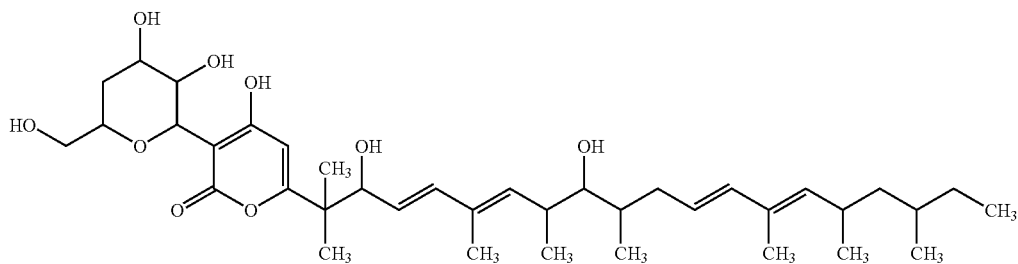

such as of formula

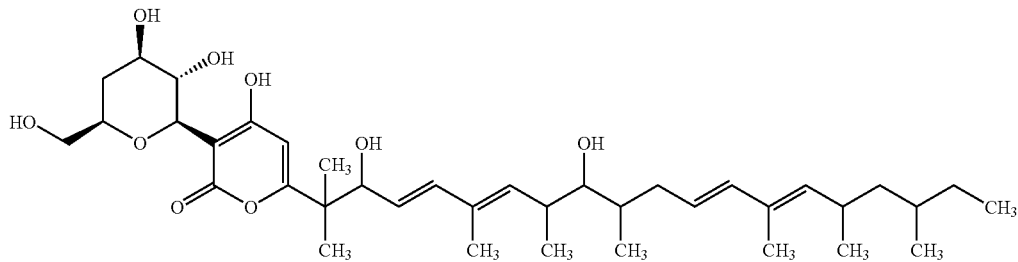

A compound of formula III includes a compound of formula III'.

Acylation may be carried out as appropriate, e.g. according, e.g. analogously, to a method as conventional. In a preferred aspect of the present invention acylation is carried out by reaction of a compound of formula II with acetic acid anhydride in organic solvent, e.g. pyridine, and isolating a compound of formula II obtained from the reaction mixture. Optionally, and if desired, salt formation of a compound of formula II may be carried out as appropriate, e.g. as described above for a compound of formula I.

A compound of formula III may be obtained as appropriate, e.g. according, e.g. analogously, to a process as conventional, e.g. e.g. by culturing a strain producing a compound of formula III, e.g. a strain of the genus Microsphaeropsis Hohn, such as the fungus strain NRRL 15684, in the presence of a culture medium and recovering a compound of formula III from the culture medium, e.g. by chromatography, see e.g. U.S. Pat. No. 4,753,959.

In an intermediate of formula II or in a compound of formula III (starting materials), functional groups, if present, optionally may be in protected form or in the form of a salt, if a salt-forming group is present. Protecting groups, optionally present, may be removed at an appropriate stage, e.g. according, e.g. analogously, to a method as conventional. Any compound described herein may be prepared as appropriate, e.g. according, e.g. analogously, to a method as conventional, e.g. or as specified herein.

The compounds of the present invention, e.g. including a compound of formula I and of formula I', exhibit pharmacological activity and are therefore useful as pharmaceuticals. In particular we have found surprisingly that the compounds of the present invention show anti-inflammatory activity and are e.g. useful in diseases associated with inflammation.

Antiinflammatory activity may be tested in test systems in vivo, e.g. as described in Example 3 below.

The compounds of the present invention show therapeutic activity and are thus useful in the treatment of diseases associated with inflammation, e.g. for use as antiinflammatory agents, e.g. for use in the treatment of inflammatory disorders, such as in suppression of neoplastic diseases, e.g. inflammatory skin diseases and autoimmune diseases, such as: psoriasis, atopic dermatitis, contact dermatitis and related eczematous dermatitises, seborrheic dermatitis, phototoxic and photoallergic dermatitis, Lichen planus, Pemphigus, bullous Pemphigoid, Epidermolysis bullosa, urticaria, angioedemas, vasculitides, erythemas, cutaneous easinophilias, Lupus erythematosus, Alopecia areata and acne.

In another aspect the present invention provides a compound of the present invention for use as a pharmaceutical, e.g. for the treatment of diseases associated with inflammation.

For pharmaceutical use a compound of the present invention includes one or more, preferably one, compounds of the present invention, e.g. a combination of two or more compounds of the present invention.

In another aspect the present invention provides the use of a compound of the present invention for the manufacture of a medicament, e.g. a pharmaceutical composition, for the treatment of diseases associated with inflammation.

The compounds of Examples 1 and 2 are preferred compounds of the present invention. The compounds of the invention may be administered in similar manner to known standards for use in the treatment of diseases associated with inflammation.

In a further aspect the present invention provides a method of treatment of diseases which are associated with inflammation, which method comprises administering to a subject in need of such treatment an effective amount, e.g. an antiinflammatory effective amount, of a compound of the present invention; e.g. in the form of a pharmaceutical composition.

Treatment includes treatment and prophylaxis.

For such treatment, the appropriate dosage will, of course, vary depending upon, for example, the chemical nature and the pharmakokinetic data of a compound of the present invention employed, the individual host, the mode of administration and the nature and severity of the conditions being treated. However, in general, for satisfactory results in larger mammals, for example humans, an indicated daily dosage is in the range from about 5 mg to about 1500 mg (ca. 0.06 mg/kg to ca. 20 mg/kg body weight), such as about 50 to about 1200 mg (ca. 4 mg/kg to ca. 15 mg/kg body weight) of a compound of the present invention; conveniently administered, for example, in divided doses up to 4 times a day. A compound of the present invention may be administered by any conventional route, for example enterally, e.g. including nasal, buccal, rectal, oral, administration; parenterally, e.g. including intravenous, intramuscular, subcutanous administration; or topically; e.g. including epicutaneous, intranasal, intratracheal administration; e.g. in form of coated or uncoated tablets, capsules, (injectable) solutions, solid solutions, suspensions, dispersions, solid dispersions; e.g. in the form of ampoules, vials, in the form of creams, gels, pastes, inhaler powder, foams, tinctures, lip sticks, drops, sprays, suppositories.

The compounds of the present invention may be administered in the form of a pharmaceutically acceptable salt, e.g. metal salt; or in free form; optionally in the form of a solvate. The compounds of the present invention in the form of a salt exhibit the same order of activity as the compounds of the present invention in free form; optionally in the form of a solvate.

A compound of the present invention may be used for pharmaceutical treatment according to the present invention alone, or in combination with one or more other pharmaceutically active agents. Such other pharmaceutically active agents include e.g. other pharmaceutically active compounds which are active in the treatment of diseases associated with inflammation, e.g. and antibacterials.

Combinations include fixed combinations, in which two or more pharmaceutically active agents are in the same formulation; kits, in which two or more pharmaceutically active agents in separate formulations are sold in the same package, e.g. with instruction for co-administration; and free combinations in which the pharmaceutically active agents are packaged separately, but instruction for simultaneous or sequential administration are given.

In another aspect the present invention provides a pharmaceutical composition comprising a compound of the present invention in association with at least one pharmaceutical excipient, e.g. appropriate carrier and/or diluent, e.g. including fillers, binders, disintegrators, flow conditioners, lubricants, sugars and sweeteners, fragrances, preservatives, stabilizers, wetting agents and/or emulsifiers, solubilizers, salts for regulating osmotic pressure and/or buffers.

In another aspect the present invention provides a pharmaceutical composition according to the present invention, further comprising another pharmaceutically active agent.

Such compositions may be manufactured according, e.g. analogously to a method as conventional, e.g. by mixing, granulating, coating, dissolving or lyophilizing processes. Unit dosage forms may contain, for example, from about 50 mg to about 1000 mg, such as 100 mg to about 500 mg.

In the following Examples all temperatures are in degrees Celsius (° C.) and are uncorrected.

The following abbreviations are used:
DMF N,N-dimethylformamide

EXAMPLE 1

Acetic acid 7-acetoxy-1-[1-(3,4-diacetoxy-4'-hydroxy-2'-oxo-6-sulfooxymethyl-3,4,5,6-tetrahydro-2.H.,2'.H.-[2,3']bipyranyl-6'-yl)-1-methyl-ethyl]-4,6,8,12,14,16-hexamethyl-octadeca-2,4,10,12-tetraenyl ester 1A. Acetic acid (2E,4E,10E,12E)-7-acetoxy-1-[1-((2R,3R,4R,6R)-3,4-diacetoxy-4'-hydroxy-6-hydroxymethyl-2'-oxo-3,4,5,6-tetrahydro-2.H.,2'.H.-[2,3']bipyranyl-6'-yl)-1-methyl-ethyl]-4,6,8,12,14,16-hexamethyl-octadeca-2,4,10,12-tetraenyl ester 5 g of (2R,3S,4R,6R)-6'-((3E,5E,11E,13E)-2,8-Dihydroxy-1,1,5,7,9,13,15,17-octamethyl-nonadeca-3,5,11,13-tetraenyl)-3,4,4'-trihydroxy-6-hydroxymethyl-3,4,5,6-tetrahydro-2-H.-[2,3']bipyranyl-2'-one, dissolved in 25 ml of pyridine and 25 ml of acetic anhydride, are stirred for 18 hours, solvent is evaporated, the evaporation residue obtained is dissolved in toluene and pyridinium salts are filtered off. From the filtrate obtained solvent is evaporated and the evaporation residue obtained is dissolved in 100 ml of $CH_3OH$. To the mixture obtained 4 ml of 33% aqueous $NH_3$ are added, the mixture obtained is stirred for 18 hours, solvent is evaporated and the evaporation residue obtained is subjected to chromatography. Acetic acid (2E,4E, 10E,12E)-7-acetoxy-1-[1-((2R,3R,4R,6R)-3,4-diacetoxy-4'-hydroxy-6-hydroxymethyl-2'-oxo-3,4,5,6-tetrahydro-2.H.,2'.H.-[2,3']bipyranyl-6'-yl)-1-methyl-ethyl]-4,6,8,12,14,16-hexamethyl-octadeca-2,4,10,12-tetraenyl ester is obtained. $^1$H-NMR ($CDCl_3/CD_3OD$ 4:1) 6.30 (d, 1H, $H_3$, J=15Hz); 6.20 (d, 1H, $H_{11}$, J=15.5 Hz); 5.91 (s, 1H, $H_5$'); 5.37-5.58 (m, 4H, $H_{1,2,5,10}$); 5.08-5.20 (m, 3H, $H_{3\text{-}pyranyl,4\text{-}pyranyl,13}$); 4.82 (d, 1H, $H_{2\text{-}pyrnyl}$, J=9.4 Hz); 4.75 (dd, 1H, H-7, J=4.4,7.8 Hz); 3.70-3.85 (m, 2H, $H_{a\text{-}acetoxymethyl}$, $H_{b\text{-}acetoxymethyl}$); 3.61 (m, 1H, $H_{6\text{-}pyranyl}$); 2.88 (m, 1H, H-6); 2.58 (m, 1H, H-14); 2.24 (m, 1H, $H\text{-}_{5a\text{-}pyranyl}$); 2.20 (m, 1H, $H_{9a}$); 2.08 (s, 3H, $COCH_3$), 2.04 (s, 3H, $COCH_3$); 2.01 (s, 3H, $COCH_3$), 2.00 (s, 3H, $COCH_3$); 1.83 (m, 1H, $H_{9b}$); 1.73-1.77 (m, 2H, $H_{5b\text{-}pyranyl}$, $H_8$); 1.73 (2xs, 6H, $CH_{3\text{-}4,12}$); 1.17-1.30 (m, 3H, $H_{15a,16,17a}$); 1.24 (s, 3H, gem-$CH_3$); 1.21 (s, 3H, gem-$CH_3$); 1.05-1.18 (m, 2H, $H_{15b,17b}$); 0.98 (d, 3H, $CH_{3\text{-}6}$, J=7 Hz); 0.93 (d, 3H, $CH_{3\text{-}14}$, J=7 Hz); 0.80-0.88 (m, 9H, $CH_{3\text{-}8,16,18}$); MS-ESI m/e 829 (MH$^+$, 100).

1B. Acetic acid (2E,4E,10E,12E)-7-acetoxy-1-[1-((2R,3R,4R,6R)-3,4-diacetoxy-4'-hydroxy-2'-oxo-6-sulfooxymethyl-3,4,5,6-tetrahydro-2.H.,2'.H.-[2,3']bipyranyl-6'-yl)-1-methyl-ethyl]-4,6,8,12,14,16-hexamethyl-octadeca-2,4,10,12-tetraenyl ester 953 mg of $SO_3$-pyridine complex are added to 1 g of acetic acid (2E,4E,10E,12E)-7-acetoxy-1-[1-((2R,3R,4R,6R)-3,4-diacetoxy-4'-hydroxy-6-hydroxymethyl-2'-oxo-3,4,5,6-tetrahydro-2.H.,2'.H.-[2,3']bipyranyl-6'-yl)-1-methyl-ethyl]-4,6,8,12,14,16-hexamethyl-octadeca-2,4,10,12-tetraenyl ester in 90 ml of DMF and the resulting solution is stirred for 12 hours. From the mixture obtained solvent is evaporated and the evaporation residue obtained is subjected to chromatography. Acetic acid (2E,4E,10E,12E)-7-acetoxy-1-[1-((2R,3R,4R,6R)-3,4-diacetoxy-4'-hydroxy-2'-oxo-6-sulfooxymethyl-3,4,5,6-tetrahydro-2.H.,2'.H.-[2,3']bipyranyl-6'-yl)-1-methyl-ethyl]-4,6,8,12,14,16-hexamethyl-octadeca-2,4,10,12-tetraenyl ester is obtained. $^1$H-NMR ($CDCl_3/CD_3OD$ 4:1, 330K) 6.28 (d, 1H, $H_3$, J=15.5 Hz); 6.03 (d, 1H, $H_{11}$, J=15.4 Hz); 5.75 (s, 1H, $H_5$'); 5.56 (d, 1H, $H_1$, J=7.6 Hz); 5.50 (d, 1H, $H_5$, J=7.5 Hz); 5.44-5.48 (m, 3H, $H_{3\text{-}pyranyl,2,10}$); 5.14 (m, 1H, $H_{4\text{-}pyranyl}$); 5.12 (d, 1H, $H_{13}$, J=9.6 Hz); 4.87 (d, 1H, $H_{2\text{-}pyranyl}$, J=11.1 Hz); 4.77 (dd, 1H, $H_7$, J=5.3,6.9 Hz); ABX-system ($\mu_A$=4.37, $H_{a\text{-}acetoxymethyl}$, $\mu_B$=4.08, $H_{b\text{-}acetoxymethyl}$, $\mu_x$=4.02, $H_{6\text{-}pyranyl}$, $J_{AB}$=10.9, $J_{AX}$=3.0, $J_{BX}$=1.9 Hz); 2.89 (m, 1H, $H_6$); 2.55 (m, 1H, $H_{14}$); 2.24 (m, 1H, $H_{9a}$); 2.20 (m, 1H, $H_{5a\text{-}pyranyl}$); 2.12 (m, 1H, $H_{5b\text{-}pyranyl}$); 2.05 (s, 3H, $COCH_3$), 2.02 (2xs, 6H, $COCH_3$); 1.90 (m, 1H, $H_{9b}$); 1.87 (s, 3H, $COCH_3$); 1.80 (m, 1H, $H_8$); 1.72 (2xs, 6H, $CH_{3\text{-}4,12}$); 1.22-1.30 (m, 3H, $H_{15a,16,17a}$); 1.23 (s, 3H, gem-$CH_3$); 1.18 (s, 3H, gem-$CH_3$); 1.13 (m, 1H, $H_{17b}$); 1.08 (m, 1H, $H_{15b}$); 0.95 (d, 3H, $CH_{3\text{-}6}$, J=6.9 Hz); 0.93 (d, 3H, $CH_{3\text{-}15}$, J=6.7 Hz); 0.82-0.87 (m, 9H, $CH_{3\text{-}8,16,18}$); MS-ESI m/e 947 (MK$^+$, 100).

EXAMPLE 2

Acetic acid (2E,4E,10E,12E)-7-acetoxy-1-[1-((2R, 3R,4R,6R)-3,4-diacetoxy-4'-hydroxy-2'-oxo-6-sulfamoyloxymethyl-3,4,5,6-tetrahydro-2.H.,2'.H.-[2,3'] bipyranyl-6'-yl)-1-methyl-ethyl]-4,6,8,12,14,16-hexamethyl-octadeca-2,4,10,12-tetraenyl ester 36 mg of NaH are added to 600 mg of acetic acid (2E,4E, 10E,12E)-7-acetoxy-1-[1-((2R,3R,4R,6R)-3,4-diacetoxy-4'-hydroxy-6-hydroxymethyl-2'-oxo-3,4,5,6-tetrahydro-2.H., 2'.H.-[2,3']bipyranyl-6'-yl)-1-methyl-ethyl]-4,6,8,12,14,16-hexamethyl-octadeca-2,4,10,12-tetraenyl ester in 18 ml of DMF and the mixture obtained is stirred for 45 minutes. To the mixture obtained 432 mg of $ClSO_2NH_2$ are added and the resulting solution is stirred for further 2 hours. From the mixture obtained solvent is evaporated, the evaporation residue is treated with ethyl acetate and the organic layer obtained is extracted with saturated sodium bicarbonate and brine. The organic layer obtained is dried, solvent is evaporated and the evaporation residue is subjected to chromatography. Acetic acid (2E,4E,10E,12E)-7-acetoxy-1-[1-((2R,3R,4R,6R)-3,4-diacetoxy-4'-hydroxy-2'-oxo-6-sulfamoyloxymethyl-3,4,5, 6-tetrahydro-2.H.,2'.H.-[2,3']bipyranyl-6'-yl)-1-methyl-ethyl]-4,6,8,12,14,16-hexamethyl-octadeca-2,4,10,12-tetraenyl ester is obtained. $^1$H-NMR (CDCl$_3$/CD$_3$OD 4:1) 6.26 (d, 1H, $H_3$, J=15.5 Hz); 6.03 (d, 1H, $H_{11}$, J=15.5 Hz); 5.77 (s, 1H, $H_5$'); 5.74 (m, 1H, $H_{3\text{-}pyranyl}$) 5.57 (d, 1H, $H_1$, J=7.5 Hz); 5.43-5.50 (m, 2H, $H_{2,10}$); 5.47 (d, 1H, $H_5$, J=7.8 Hz ); 5.10 (d, 1H, $H_{13}$, J=9.3 Hz); 5.09 (m, 1H, $H_{4\text{-}pyranyl}$); 4.80 (m, 1H, $H_{2\text{-}pyranyl}$); 4.76 (dd, 1H, $H_7$, J=4.6,7.6 Hz); ABX-system ($\mu_A$=4.37, $H_{a\text{-}acetoxymethyl}$, $\mu_B$=4.20, $H_{b\text{-}acetoxymethyl}$, $\mu_x$=3.90, $H_{6\text{-}pyranyl}$, $J_{AB}$=11.9, $J_{AX}$=2.5, $J_{BX}$=4.6 Hz); 2.90 (m, 1H, $H_6$); 2.58 (m, 1H, $H_{14}$); 2.23 (m, 1H, $H_{9a}$); 2.14 (m, 1H, $H_{5a\text{-}pyranyl}$); 2.07 (s, 3H, $COCH_3$), 2.03 (s, 3H, $COCH_3$); 2.02 (s, 3H, $COCH_3$); 1.93 (m,1H, $H_{5b\text{-}pyranyl}$); 1.89 (s, 3H, $COCH_3$); 1.87 (m, 1H, $H_{9b}$); 1.79 (m, 1H, $H_8$); 1.74 (2xs, 6H, $CH_{3\text{-}4,12}$); 1.22-1.32 (m, 3H, $H_{15a,16,17a}$); 1.23 (s, 3H, gem-$CH_3$); 1.19 (s, 3H, gem-$CH_3$); 1.13 (m, 1H, $H_{17b}$); 1.08 (m, 1H, $H_{15b}$); 0.96 (d, 3H, $CH_{3\text{-}6}$, J=7 Hz); 0.93 (d, 3H, $CH_{3\text{-}15}$, J=6.9 Hz); 0.82-0.87 (m, 9H, $CH_{3\text{-}8,16,18}$); MS-ESI m/e 908 (MH$^+$, 50).

EXAMPLE 3

Antiinflammatory Activity

Antiinflammatory activity may be tested in test systems in vivo, namely in the IL-8 induced leucocytes emigration model, in the Topical ICD-TPA mouse model and in the ACD mouse model, e.g. as described below, wherein the following abbreviations are used:

ACD allergic contact dermatitis

DAE mixture of acetylacetamide, ethanol and acetone

ICD isocitric dehydrogenase

IL-8 interleukin-8

PBS phosphate buffered saline

TPA 12-O-tetradecanoyl phorbol-13-acetate (phorbol-12-myristate)

Test compounds include compounds of the present invention of formula I, namely of formula I'.

Test Systems a. IL-8 Induced Leucocytes Emigration Model

Comprise 24 to 36 female Balb/c mice, 18-20 g; IL-8 control group; reference group; buffer control group and 3 to 6 test groups. Human recombinant IL-8 is injected at 1 μg in 100 μl PBS i.p..

5 mg of a test compound, or reference compound, respectively, are dissolved in 1 ml of PBS. Immediately after i.p. injection of IL-8 100 μl of the test compound-solution are injected i.v. (=500 μg/mouse). 4 hours after IL-8 injection the mice are anaesthetized and blood is collected by orbital puncture. The mice are sacrificed and peritoneal exudate cells harvested as follows: 5 ml of PBS are injected i.p. and after 1 minute as much of it as possible is recovered. Total cell counts of blood and peritoneal cells are performed on the Toa-Counter (Coulter).

The cytospin preparation is done on the Shandon Cytocentrifuge "Cytospin" 2. The blood smears and cytospin preparations are stained with Hemacolor (Merck). Differential cell counts of blood smears and peritoneal cells are performed under the microscope. Statistical evaluation (t-test) of the results is performed.

The compounds of the present invention show activity in the IL-8 induced leucocytes emigration model.

b. Topical ICD-TPA Mouse Model (TPA-Induced Irritant Contact Dermatitis)

10 μl of a 0.01% TPA solution is epicutaneously applied to the inner surface of the right ear of 8 NMRI mice per group for elicitation of an inflammatory pinnal swelling. The test animals are treated topically with 10 μl of a test compound (dissolved in DAE) 30 minutes before the application of TPA; control animals are treated similarly with the vehicle DAE alone. 6 hours after TPA-treatment the animals are sacrificed, both ear lobes cut off at the basis and weighed. Difference in auricular weights are taken as a measure of inflammatory swelling [right (treated, irritated) vs left (untreated, non irritated) ears, in %]. The compounds of the present invention show activity in the ICD-TPA model.

c. Topical ACD-Model (Oxazolone-Sensitized Mice)

10 μl of 2% oxazolone are epicutaneously applied to the inner surface of the right ear of 8 NMRI mice per group which mice are sensitized against oxazolone. After 30 minutes the test animals are treated topically with 10 μl of a test compound (dissolved in DAE). 24 hours later the animals are sacrificed. Inflammatory swelling is measured as set out under point "b. Topical ICD-TPA mouse model" above. The compounds of the present invention show activity in the topical ACD model.

The invention claimed is:
1. A compound of formula

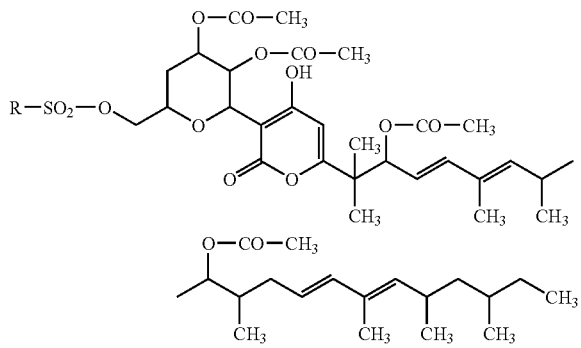

wherein R is hydroxy or amino.
2. A compound of claim 1 wherein R is hydroxy.
3. A compound of claim 1, wherein R is amino.
4. A compound of claim 1 in the form of a salt.
5. A compound of claim 4 in the form of an alkali salt.
6. A compound of claim 5, which is a sodium salt.
7. A compound of claim 6 wherein R is amino.
8. A pharmaceutical composition comprising a compound of claim 1 in combination with at least one pharmaceutically acceptable excipient.
9. A method of treatment of inflammation associated with a disease which treatment comprises administering to a subject in need of such treatment an effective amount of a compound of claim 1.
10. The method of claim 9 wherein said disease is selected from psoriasis, atopic dermatitis, contact dermatitis and related eczematous dermatitises, seborrheic dermatitis, phototoxic and photoallergic dermatitis, Lichen planus, Pemphigus, bullous Pemphigoid, Epidermolysis bullosa, urticaria, angioedemas, vasculitides, erythemas, cutaneous easinophillias, Lupus erythematosus, Alopecia areata and acne.
11. The method of claim 9 wherein the amount of compound administered is about 0.06 mg/kg to about 20 mg/kg body weight per day.

* * * * *